United States Patent [19]

Dubois et al.

[11] Patent Number: 4,474,679
[45] Date of Patent: Oct. 2, 1984

[54] DIPHENYL BENZOATES AND ITS USE AS A DOPANT FOR SMECTIC LIQUID CRYSTALS

[75] Inventors: Jean C. Dubois; Pierre Le Barny; Jean P. Billard; Lydie Thirant; Serge Le Berre; Annie Beguin, all of Paris, France

[73] Assignee: Thomson-CSF, Paris, France

[21] Appl. No.: 424,616

[22] Filed: Sep. 27, 1982

[30] Foreign Application Priority Data

Dec. 31, 1981 [FR] France .................... 81 24563

[51] Int. Cl.$^3$ ............................ C09K 3/34; G02F 1/13
[52] U.S. Cl. ...................... 252/299.65; 260/465 D; 350/350 R; 560/73; 560/108
[58] Field of Search ............ 260/465 D; 560/73, 108; 252/299.66, 299.65; 350/350 R

[56] References Cited

U.S. PATENT DOCUMENTS 4,029,594  6/1977  Gavrilovic .................... 252/299
4,112,239  9/1978  Dubois et al. ................. 560/73
4,235,736  11/1980 Beguin et al. ................. 252/299

FOREIGN PATENT DOCUMENTS 11002    5/1980  European Pat. Off. .
2179180  11/1973 France .
2297201  8/1976  France .

Primary Examiner—Dolph H. Torrence
Attorney, Agent, or Firm—Oblon, Fisher, Spivak, McClelland & Maier

[57] ABSTRACT

The invention relates to an organic compound obtained by synthesis from 3,5-dihydroxybenzoic acid. The compound according to the invention is in accordance with the following general formula:

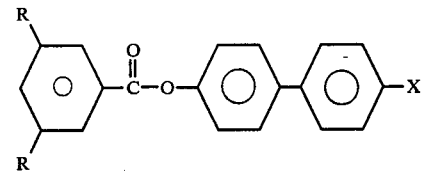

in which R stands for an organic group of the alkyl, alkoxy or alkyl carboxylate type having 1 to 15 carbon atoms and in which X designates a nitrile or halogene group.

6 Claims, No Drawings

DIPHENYL BENZOATES AND ITS USE AS A DOPANT FOR SMECTIC LIQUID CRYSTALS

BACKGROUND OF THE INVENTION

The use of smectic A liquid crystals in display means using a mixed thermal and electrical effect is now well known. Among the materials which can be used for this purpose are diphenyl derivatives such as 4-cyano-4'-octyl diphenyl, which has a smectic A phase and a nematic phase. Other patents of the present Applicant relate to smectic A materials with or without a nematic phase during smectic-isotropic phase transitions. The present invention relates to dopants for incorporating into these materials. In particular, these dopants lead to an increase in contrast, a reduction of the control power and also a reduction of the video voltage.

BRIEF SUMMARY OF THE INVENTION

The present invention more particularly relates to dopants usable with smectic liquid crystals in thermooptical display means with or without the assistance of an electrical control field. The smectic material obtained after adding one or more dopants according to the invention may or may not have a nematic phase.

These dopants, formed from organic compounds, are in accordance with the following general formula:

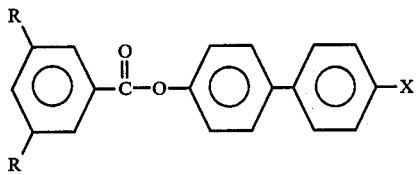

in which R represents an organic group of the alkyl, alkoxy or alkyl carboxylate (ester) type having 1 to 15 carbon atoms and in which X designates a nitrile radical or halogen.

These substances are, for example, designated by expressions of the type 3,5-dialkyl or dialkoxydiphenyl-p-cyano or p-halobenzoate.

Hereinafter, a general process for the preparation of these substances is given, followed by a description of the operating procedure of certain characteristic stages for a particular case. An example will now be given of the application to the display by smectic liquid crystal systems.

GENERAL PREPARATION PROCEDURE

The dopants can be prepared from a basic substance such as 3,5-dihydroxybenzoic acid of formula:

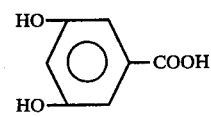

(1) Esterification of the 3,5-dihydroxybenzoic acid in order to obtain methyl-3,5-dihydroxybenzoate of formula:

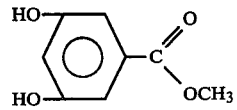

(2) Alkylation of the above product to fix the R radical and obtain a product with the following general formula:

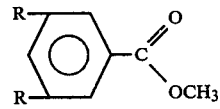

(3) Acidification of the above product to obtain the following compound:

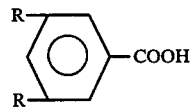

(4) Chlorination of the previously prepared acid to obtain the acid chloride:

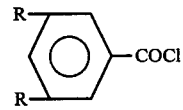

(5) Esterification from the acid chloride to obtain the end product:

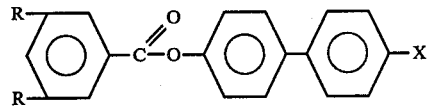

In exemplified manner will be given the operating procedure for a dopant according to the invention: 4'cyano 4"(3,5 dioctyloxy) benzoyloxy diphenyl.

OPERATING PROCEDURE (1) Synthesis of methyl-3,5-dihydroxybenzoate 5.9 g of 3,5-dihydroxybenzoic acid is dissolved into 50 ml of ethyl ether in an 250 ml Erlenmeyer flask, equipped with a magnetic stirrer. This is followed by the addition of an ethereal diazomethane solution prepared according to a known method (Vogel's Text Book of Practical Organic Chemistry, fourth edition Longman, London and New York, p.291) until the characteristic yellow colouring of a diazomethane excess is obtained. A precipitate appears, which is separated from the reaction medium by filtration. The filtrate is evaporated by vacuum drying. The crude product is dissolved in a mixture of 90 parts chloroform and 10 parts methanol and then precipitated by petroleum ether. This is followed by filtration and vacuum drying. 5.17 g of ester I is obtained and the yield of this reaction is 80%.

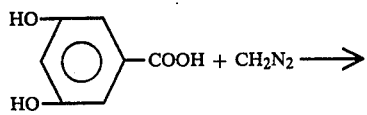

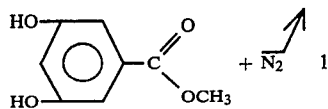

(2) Synthesis of methyl-3,5-dioctyloxybenzoate 200 ml of ethyl alcohol and then 2.3 g of purified sodium are introduced into a 500 ml Erlenmeyer flask. A reflux condenser is fitted to the Erlenmeyer flask and the reaction medium is stirred with a magnetized bar. When the sodium ethylate is formed, 8.4 g of methyl-3,5-dihydroxybenzoate is added, accompanied by stirring. As soon as the medium has become homogeneous, 20.26 g of distilled octyl bromide are added dropwise. Heating under refluxing takes place for 20 hours.

The reaction medium is transferred into a 500 ml round-bottomed flask and the ethyl alcohol is distilled. This is followed by the addition of 100 ml of soft water and distillation takes place until a temperature of 100° C. is obtained in the vapours. The ester II is extracted with ether and then purified by liquid chromatography (eluent 50 parts hexane and 50 parts toluene), the melting point being 36.5° C. The yield of this reaction is 30%.

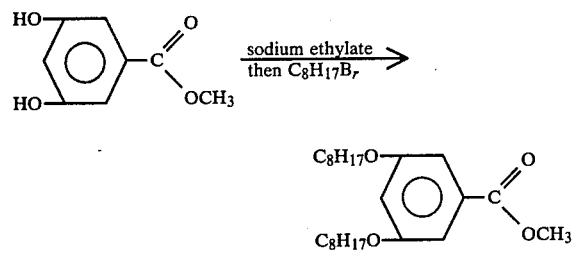

(ester II)

(3) Synthesis of 3,5-dioctyloxybenzoic acid 39 g of potash are dissolved hot in 400 ml of ethyl alcohol in a 1 liter round-bottomed flask, followed by the addition of 12.5 g of ester II and heating under reflux for 2 hours. The reaction mixture is concentrated in a vacuum and water is added, followed by the acidification of the thus obtained aqueous phase. The acid III is extracted with ethyl ether and then recrystallized in alcohol at −18° C. The yield of the method is 90%.

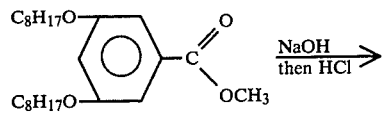

-continued

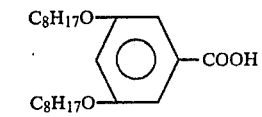

(acid III)

(4) Synthesis of 3,5-dioctyloxybenzoic acid chloride

The acid III is converted into acid chloride IV by refluxing the thionyl chloride.

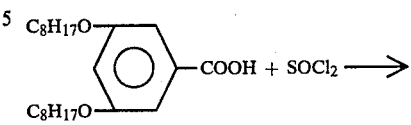

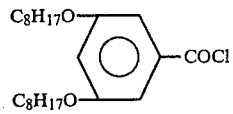

(5) Synthesis of 4' cyano 4''(3,5 dioctyloxy)benzoyloxy diphenyl

A solution of 5.67 g of 4-hydroxy-4'-cyanodiphenyl in 40 ml of pyridine is introduced into a 100 ml round-bottomed flask containing 11.5 g of acid chloride IV. This is followed by stirring for 48 hours at ambient temperature. The reaction mixture is poured onto 200 g of ice, followed by acidification at pH 3 and extraction of the ester V with ether. The ethereal phase is washed with water and then dried. The ester is purified by liquid chromatography under pressure (eluent: toluene) then by recrystallization in ethanol (m.p. 86.5° C.). The yield of this method is 60%.

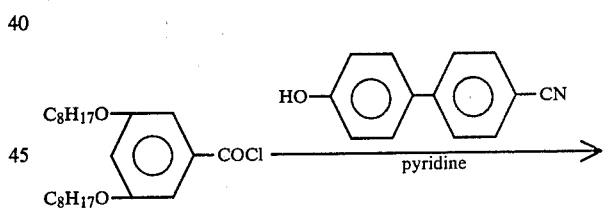

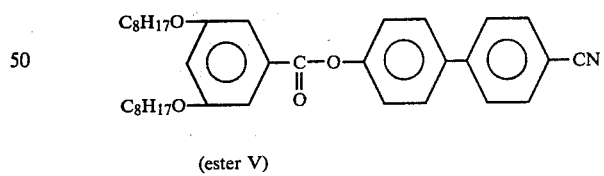

(ester V)

On introducing a dopant in accordance with the aforementioned general formula into smectic liquid crystals, there is found to be a modification of the optical qualities thereof. In display means, these dopants lead to an increase in contrast, a reduction of the control power and a reduction of the video voltage. They can be used in thermooptical devices with or without the assistance of the electrical field. It is advantageous to use them in devices utilizing the mixed thermal and the electrical effect. The introduction of one or more dopants into a smectic liquid crystal, as from a certain percentage, leads to the suppression of the nematic phase. However, the new material obtained in this way can still be controlled by an electrical field during the passage from the isotropic phase to the smectic phase and this applies with respect to control voltages below those used for the same basic smectic material without dopants.

As a non-limitative example, the aforementioned dopant, whose preparation has been described, can be used with 4-cyano-4'-octyldiphenyl, this being a smectic liquid crystal frequently employed in display means. The phase transitions of this liquid crystal are K 21.5 $S_A$ 33.5 N40.5 I (the temperatures being given in °C.).

When the dopant in question, 4' cyano 4"(3,5 dioctyloxy) benzoyloxy diphenyl, is introduced into this liquid crystal, the phase transitions are modified in accordance with the phase diagram of the attached drawing. The ordinates of this diagram relate to temperature (from $-10°$ to $+90°$ C.). The abscissa gives the dopant weight from 0 to 100% in the liquid crystal-dopant mixture. For ordinate A, the crystal contains 0% of dopant and for ordinate B, it contains 100% of dopant.

On this diagram, it is possible to see the phase transitions of the basic smectic material (4-cyano-4'-octyldiphenyl) without dopant and these are the points C (21.5° C.), D (33.5° C.) and E (40.5° C.). It can be seen that the higher the dopant percentage therefore in the liquid crystal-dopant mixture, the more the nematic phase amplitude decreases and is suppressed at about 5% dopant (line zz' from the abscissa axis).

The contrast in this type of display means increases in proportion to the quantity of dopant introduced. The increase in the contrast as a function of the dopant percentage can be explained by analogy with the crystallization phenomenon from nuclei. The introduction of appropriate dopants into a smectic liquid crystal leads to a multiplication of the defects within the material, which has the effect of reducing the size of the diffusing areas and consequently increases contrast. In practice, the dopant proportions added vary from 1% to larger proportions of approximately 15%, when this doped product is used in matrix access display means. The contrast obtained is multiplied by a factor of 2 or 3 (for the highest dopant concentrations) and the video voltage is reduced in the same ratio. The control power necessary for heating the liquid crystal in order to make it pass from the smectic phase to the isotropic phase is reduced through then reducing the temperature amplitude of the nematic phase or even by its elimination.

The form of the molecule of the organic compound serving as the dopant has a determinative action within the smectic liquid crystal where it is introduced, particularly due to the nature of the organic groups R.

Similar results are obtained with a mixture of liquid crystals, which is also given in an exemplified manner:

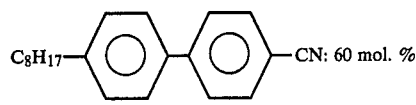 CN: 60 mol. %

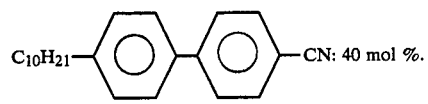 CN: 40 mol %.

This mixture has the following phase transitions: K9$S_A$42.9 N44.8 I. A dopant according to the invention is incorporated into this, i.e. 4' cyano 4"(3,5 dioctyloxy) benzoyloxy diphenyl in order to reduce the temperature amplitude of the nematic phase. The transition temperatures are modified in the manner indicated in the following table, where the temperatures were recorded during the heating of the doped mixture from the smectic phase to the isotropic phase.

| % by weight dopant | $S_A$ | N | I |
|---|---|---|---|
| 0 | . | 42.9 . | 44.8 . |
| 2 | . | 42.4 . | 43.6 . |
| 5 | . | 41.4 . | 42 . . |
| 7.5 | . | 40.5 | . |
| 10 | . | 40.2 | . |

Without dopant, the mixture has a nematic phase with a temperature amplitude of 1.9° C. The addition of the dopant has the effect of reducing this amplitude to 1.2° C. for 2% by weight dopant in the doped mixture and 0.6° C. for 5% dopant. As from 7.5% dopant, the nematic phase is eliminated. As hereinbefore, the contrast obtained in the thermooptical devices also increases as a function of the dopant proportion.

It also falls within the scope of the present invention to use the compound according to the invention in smectic liquid crystal display means only using the thermal effect for controlling the orientation of molecules, e.g. using an intensity-modulated laser beam.

The organic compound according to the invention makes it possible to dope smectic liquid crystals in order to reduce the temperature amplitude of the nematic phase and even suppress it, whilst retaining the possibility of using these smectic materials in display means having a mixed thermal and electrical effect. The introduction of this dopant leads to the triple advantage of increase in the contrast, reducing the control power and reducing the video voltage.

What is claimed is:

1. An organic compound having the following formula:

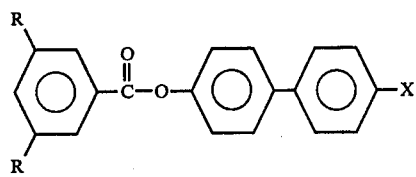

in which R represents an alkoxy group of the formula $C_nH_{2n+1}O$ in which n is an integer ranging from 1 to 15 and X is a nitrile or halogen radical.

2. An organic compound according to claim 1 wherein R is $C_8H_{17}O$ and X is CN.

3. A method for reducing the temperature amplitude of the nematic phase in smectic liquid crystals, even to suppression thereof, which comprises adding an effective amount of a dopant of the formula:

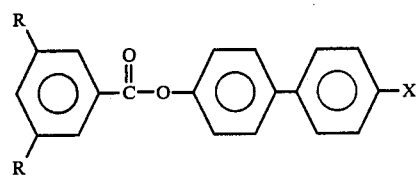

wherein R is an alkoxy group of the formula $C_nH_{2n+1}O$, in which n is an integer ranging from 1 to 15 and X is a nitrile or halogen radical, to smectic liquid crystals.

4. The method of claim 3, wherein the dopant for said smectic liquid crystals effects the elimination of the nematic phase during the smectic-isotropic phase transition.

5. The method of claim 3, wherein said doped smectic liquid crystals are used in display devices, thereby providing increased contrast, control power reduction and video voltage reduction in said display devices.

6. The method of claim 5, wherein in said display devices, said dopant comprises 1 to 15% by weight of said doped product based on the total weight.

* * * * *